(12) United States Patent
Afriat

(10) Patent No.: US 6,503,520 B1
(45) Date of Patent: *Jan. 7, 2003

(54) WATER-IN-OIL EMULSION CONTAINING FIBERS AND THE USE THEREOF AS A COSMETIC COMPOSITION

(75) Inventor: Isabelle Afriat, Paris (FR)

(73) Assignee: L'Oreal, Paris (FR)

( * ) Notice: Subject to any disclaimer, the term of this patent is extended or adjusted under 35 U.S.C. 154(b) by 11 days.

This patent is subject to a terminal disclaimer.

(21) Appl. No.: 09/689,768

(22) Filed: Oct. 13, 2000

(30) Foreign Application Priority Data

Oct. 15, 1999 (FR) .............................. 99 12911

(51) Int. Cl.⁷ .......................... A61K 6/00; A61K 7/00; A61K 31/74; A61K 31/695; A01N 55/00

(52) U.S. Cl. ................. 424/401; 424/78.03; 514/63; 514/762; 514/937

(58) Field of Search .................. 424/401, 59, 70.1, 424/78.03; 514/63, 762, 937

(56) References Cited

U.S. PATENT DOCUMENTS

| | | | |
|---|---|---|---|
| 4,659,562 A | | 4/1987 | Arraudeau et al. |
| 4,720,353 A | | 1/1988 | Bell |
| 5,250,289 A | | 10/1993 | Boothroyd et al. |
| 5,362,482 A | | 11/1994 | Yoneyama et al. |
| 5,498,407 A | * | 3/1996 | Atlas .................... 424/70.7 |
| 5,523,091 A | | 6/1996 | Pastour et al. |
| 5,578,641 A | | 11/1996 | Jackson et al. |
| 5,665,368 A | | 9/1997 | Lentini et al. |
| 5,777,091 A | | 7/1998 | Kuhn et al. |
| 5,851,539 A | * | 12/1998 | Mellul et al. ............... 424/401 |
| 5,863,544 A | | 1/1999 | Wilcox et al. |
| 5,871,762 A | | 2/1999 | Venkitaraman et al. |
| 5,935,589 A | | 8/1999 | Mukherjee et al. |
| 5,939,054 A | | 8/1999 | Msika et al. |
| 5,942,213 A | | 8/1999 | Bara et al. |
| 5,961,998 A | | 10/1999 | Arnaud et al. |
| 5,965,146 A | * | 10/1999 | Franzke et al. ............ 424/401 |
| 5,972,315 A | | 10/1999 | Voss et al. |
| 6,015,548 A | | 1/2000 | Siddiqui et al. |
| 6,051,211 A | | 4/2000 | Hansenne et al. |
| 6,106,818 A | | 8/2000 | Dulog et al. |
| 6,190,678 B1 | * | 2/2001 | Hasenoehri et al. ........ 424/401 |

FOREIGN PATENT DOCUMENTS

| | | |
|---|---|---|
| EP | 0 152 953 A2 | 8/1985 |
| EP | 0 268 164 | 5/1988 |
| EP | 667 146 | 1/1995 |
| EP | 0 838 210 A2 | 4/1998 |
| EP | 0 336 900 A | 10/1998 |
| EP | 10287523 | 10/1998 |
| FR | 7-196440 | 8/1995 |
| JP | 7 196440 A | 8/1995 |
| JP | A7-196440 * | 8/1995 |
| WO | 98/50005 | 11/1998 |

OTHER PUBLICATIONS

Concise Encyclopedia of Chemistry, 1994, p. 651.
Hawley's Condensed Chemical Dictionary, 1997, p. 753.
Patent Abstracts of Japan, Publication No. 10287523, date—Oct. 27, 1998, "Cosmetic For Eyebrow", English Abstract Only.
Patent Abstracts of Japan, Publication No. 62238211, date–Oct. 19, 1987, "Cosmetic for Skin Care", English Abstract Only.

* cited by examiner

Primary Examiner—Russell Travers
Assistant Examiner—Lauren Q. Wells
(74) Attorney, Agent, or Firm—Oblon, Spivak, McClelland, Maier & Neustadt, P.C.

(57) ABSTRACT

A composition in the form of a water-in-oil emulsion containing fibers, at least one silicone surfactant and-at least one wax.

The composition obtained has very good stability and can in particular constitute a cosmetic composition.

The invention also relates to the use of the said composition, in particular for caring for, treating, making up or cleansing the skin the lips, the eyelashes and/or the hair.

28 Claims, No Drawings

WATER-IN-OIL EMULSION CONTAINING FIBERS AND THE USE THEREOF AS A COSMETIC COMPOSITION

PRIORITY

This application claims priority to French Application, FR 9912911, filed Oct. 15, 1999.

BACKGROUND OF THEE INVENTION

1. Field of the Invention

The present invention relates to a composition in the form of a water-in-oil (W/O) emulsion containing fibers, at least one silicone surfactant and at least one wax, and to the use of this composition, in particular for caring for, treating and/or making up body or facial skin, the hair, the eyelashes and/or the lips of a human.

2. Description of the Background

JP 07-196 440 describes cosmetic compositions containing short polyamide fibers which impart to the compositions a velvety feel and good cosmetic behaviour. However, the incorporation of these polyamide fibers into water-in-oil (W/O) emulsions poses problems of stability, i.e. the emulsions dephase at room temperature or at higher temperatures, and do so, in particular, when the amount of fibers contained therein is large.

Thus, a need exists for W/O emulsions containing fibers, which are stable while at the same time exhibit good cosmetic properties and thus avoid the drawbacks noted above.

SUMMARY OF THE INVENTION

Accordingly, it is an object of the present invention to provide water-in-oil emulsions containing fibers, which are stable and cosmetically pleasant, i.e. soft and non-greasy, wherein a large amount of fibers can be incorporated thereinto without compromising stability and cosmetic pleasantness, including good feel and cosmetic behavior.

In particular, the present invention provides a composition in emulsion form, containing in a physiologically acceptable medium, an aqueous phase dispersed in an oily phase, which contains fibers, at least one silicone surfactant, and at least one wax.

DETAILED DESCRIPTION OF THE PREFERRED EMBODIMENTS

The present invention provides a composition in emulsion form containing, in a physiologically acceptable medium, an aqueous phase dispersed in an oily phase, wherein it contains fibers, at least one silicone surfactant and at least one wax.

The expression "physiologically acceptable medium" means a medium which is compatible with the skin, the lips, the nails, the scalp and/or the hair of a mammal, particularly a human.

The composition obtained according to the present invention has good stability over time, even at temperatures above room temperature (for example 45° C.). The composition of the present invention has the appearance of a cream, i.e. supple product as opposed to a solid product, and has a velvety texture which feels pleasant when applied. This appearance and texture may be described collectively as "cosmetic pleasantness."

The fibers which may be used in the present composition can be fibers of synthetic or natural, and inorganic or organic origin. They can be short or long, individual or organized, for example in bundles. They can have any shape, and, in particular, a circular or polygonal (square, hexagonal or octagonal) cross section depending on the specific application envisaged. However, the fibers of the present invention have blunt and/or rounded ends, and not sharp ends, to prevent injury.

In particular, the fibers of the present invention have a length ranging from 1 nm to about 20 mm, preferably from about 10 nm to 5 mm, and better still from about 0.1 mm to 1.5 mm. Their cross section can be within a circle of diameter ranging from about 2 nm to 100 $\mu$m, preferably ranging from about 20 nm to 20 $\mu$m, and better still from about 5 $\mu$m to 50 $\mu$m. The weight of the fibers may be given in denier or decitex.

The fibers of the present invention may be those used in the manufacture of textiles, and in particular silk, cotton, wool or flax fibers, cellulose fibers extracted, in particular, from wood, plants or algae, polyamide (Nylon®), rayon or viscose fibers, acetate fibers, in particular rayon acetate, cellulose acetate or silk acetate fibers, poly-p-phenylene terephthamide fibers, in particular Kevlar® fibers, acrylic fibers, in particular polymethyl methacrylate or poly-2-hydroxyethyl methacrylate fibers, polyolefin fibers and, in particular, polyethylene or polypropylene fibers, glass, silica or aramid fibers, carbon fibers, in particular, in graphite form, Teflon, insoluble collagen, polyester, polyvinyl chloride or polyvinylidene chloride, polyvinyl alcohol, polyacrylonitrile, chitosan, polyurethane or polyethylene phthalate fibers, fibers formed from a mixture of polymers such as those mentioned above, for instance polyamide/polyester fibers, and mixtures of these fibers.

It is also possible to use surgical fibers, such as resorbable synthetic fibers prepared from glycolic acid and from caprolactone ("Monocryl" from the company Johnson & Johnson), resorbable synthetic fibers such as the copolymer of lactic acid and of glycolic acid ("Vicryl" from the company Johnson & Johnson), terephthalic polyester fibers ("Ethibond" from the company Johnson& &Johnson) and stainless steel threads ("Steel" from the company Johnson & Johnson).

Moreover, the fibers of the present invention may be optionally surface-treated and be optionally coated. As coated fibers which can be used in the present invention, mention may be made of polyamide fibers coated with copper sulphide for an antistatic effect (for example the R-STAT fibers from the company Rhodia) or another polymer allowing a particular organization of the fibers (specific surface treatment) or a surface treatment which induces colour/hologram effects ("Lurex" fibre from the company Sildorex, for example).

The fibers which can be used in the composition according to the present invention are preferably polyamide or poly-p-phenylene terephthamide fibers. Their length can range from about 0.1 to 5 mm, preferably from about 0.25 to 1.6 mm, and their average diameter can range from about 5 to 50 $\mu$m. In particular, the polyamide fibers sold by Etablissements P. Bonte under the name Polyamide 0.9 Dtex 0.3 mm, having an average diameter of 6 $\mu$m, a weight of about 0.9 dtex and a length ranging from 0.3 mm to 1.5 mm, can be used. Poly-p-phenylene terephthamide fibers with an average diameter of 12 $\mu$m and a length of about 1.5 mm can also be used, such as those sold under the name Kevlar Floc by the company Du Pont Fibers.

The fibers can be present in the composition according to the present invention in an amount ranging from about 0.1 to 20% by weight and preferably from about 0.5 to 12% by weight relative to the total weight of the composition. Notably, the present invention enables a larger amount of fibers to be used in the composition than does JP 07-196 440.

As silicone surfactants which may form part of the composition according to the present invention, mention may be made of dimethicone copolyols and alkyldimethicone copolyols. Dimethicone copolyols which may be mentioned, for example, are the mixture of dimethicone copolyol, cyclomethicone and water (10/88/2) sold by the company Dow Coming under the name DC3225C or DC2-5225C, and the mixture of dimethicone copolyol and cyclopentasiloxane (85/15) sold under the name Abil EM-97 by the company Goldschmidt. Alkyldimethicone copolyols which may be mentioned in particular are those having an alkyl radical containing from about 10 to 22 carbon atoms, such as cetyl dimethicone copolyol, for instance the product sold under the name Abil EM-90 by the company Goldschmidt; lauryl dimethicone copolyol and, for example, the mixture of about 91% lauryl dimethicone copolyol and about 9% isostearyl alcohol, sold under the name Q2-5200 by the company Dow Corning, and mixtures of these silicone surfactants. The silicone surfactant is preferably an alkyldimethicone copolyol and in particular cetyldimethicone copolyol.

The amount of silicone surfactant(s) in the composition of the invention preferably ranges from about 0.1 to 5% by weight of active material, and more preferably from about 0.5 to 2% by weight of active material, relative to the total weight of the composition.

The composition of the present invention contains at least one wax which is usually present in the oily-phase of the emulsion. A wax generally has astartingmelting point of greater than or equal to 45° C. In the present description, the expression "starting melting point" means the temperature at which a wax begins to melt. This temperature can be determined by DTA (differential thermal analysis), which makes it possible to obtain the thermogram (or melting curve) for the wax under consideration. The starting melting point corresponds to the temperature at which an appreciable change in the slope of the thermogram is observed. The melting point, for its part, represents the minimum point of the thermogram.

As examples of waxes which can be used in the composition of the present invention, mention may be made of mineral waxes such as microcrystalline waxes, paraffin, petrolatum, petroleum jelly, ozokerite and montan wax; animal waxes such as beeswax and lanolin and its derivatives; plant waxes such as candelilla wax, ouricury wax, carnauba wax, Japan wax, cocoa butter, cork fiber wax or sugar cane wax; hydrogenated oils that are solid at 25° C., such as hydrogenated jojoba oil; fatty esters and glycerides that are solid at 25° C.; synthetic waxes such as polyethylene waxes and the waxes obtained by Fischer-Tropsch synthesis; silicone waxes, and mixtures thereof.

Polyethylene wax and hydrogenated jojoba oil, and mixtures thereof, are preferably used as wax.

The amount of wax(es) in the composition of the prevent invention preferably ranges from about 0.5% to 10% and more preferably from about 1.5% to 7% by weight relative to the total weight of the composition.

The oily phase of the composition according to the present invention can contain, besides the wax or waxes, oils and fatty substances of any kind that are well known to those skilled in the art, for example oils of plant origin (jojoba, avocado, sesame, sunflower, corn, soybean, safflower or grape seed oil), mineral oils (petroleum jelly or optionally hydrogenated isoparaffins), synthetic oils (isopropyl myristate, cerearyl octanoate, polyisobutylene, ethylhexyl palmitate or alkyl benzoates), volatile or non-volatile silicone oils and fluoro or fluorosilicone oils, as well as mixtures of these oils.

Preferably, the oily phase of the composition of the present invention comprises at least one silicone oil which can be present in an amount ranging, for example, from about 5 to 50% by weight and preferably from about 9 to 30% by weight relative to the total weight of the composition. Silicone oils which may be mentioned, for example, are volatile silicone oils such as cyclodimethylsiloxanes or cyclomethicones, for instance pentacyclomethicone, tetracyclomethicone or hexacyclomethicone; non-volatile silicone oils such as polydimethylsiloxanes (PDMS). The composition of the invention preferably contains at least one volatile silicone oil.

The oily phase can also contain other fatty constituents such as fatty alcohols, for instance stearyl alcohol, cetyl alcohol or cetearyl alcohol, fatty acids, gums and in particular silicone gums, for instance the mixture PDMS containing α,ω-hydroxyl groups/PDMS 5 cst (12/88) sold under the name DC 1503 by the company Dow Corning.

The oily phase is present in the composition according to the invention in an amount generally ranging from about 10 to 50% and preferably from about 12 to 40% by weight relative to the total weight of the composition, this amount comprising the amount of silicone surfactant.

The aqueous phase of the present composition of the invention can range from about 30 to 85% by weight and preferably from about 40 to 75% by weight relative to the total weight of the composition, and can contain, besides water, solvents such as primary alcohols containing from 1 to 4 carbon atoms, such as ethanol, or polyols such as butylene glycol. The solvent(s) can be present in an amount ranging from about 0.1 to 30% by weight relative to the total weight of the composition.

The composition of the present invention can also contain lipophilic gelling agents such as clays such as, for example, bentones; elastomeric polyorganosiloxanes such as, for example, those sold under the names KSG 6 from Shin-Etsu, Trefil E-505C or Trefil E-506C from Dow Corning, Gransil (SR-CYC, SR DMF10, SR-DC556) from Grant Industries, or those sold in the form of preconstituted gels: KSG 15, KSG 17, KSG 16 and KSG 18 from Shin-Etsu, Gransil SR 5CYC gel, Gransil SR DMF 10 gel and Gransil SR DC556 gel from Grant Industries, 1229-02-167 and 1229-02-168 from General Electric. A mixture of these commercial products can also be used.

The composition of the present invention has the appearance of a cream and can in particular constitute a cosmetic or dermatological composition. In this case, it finds its application in a large number of treatments, in particular cosmetic treatments of the skin, including the scalp, the hair, the nails, and/or mucous membranes, in particular for caring for, cleansing, making up and/or sun-protecting the skin and/or mucous membranes.

Thus, a subject of the present invention is the cosmetic use of the composition as defined above, for treating, protecting, caring for, removing make-up from and/or cleansing the skin, the lips and/or the hair, and/or for making up the skin and/or the lips.

Another subject of the present invention is a cosmetic treatment process for the skin, including the scalp, the hair and/or the lips, characterized in that a composition as defined above is applied to the skin, the hair and/or the lips.

In a known manner, the composition of the invention can also contain adjuvants that are common in cosmetics and/or dermatology, such as active agents, preserving agents, antioxidants, complexing agents, pH modifiers (acids or bases), fragrances, fillers (polyethylene), bactericides, odour absorbers, dyestuffs (dyes and pigments) or lipid vesicles. The amounts of these various adjuvants are those conventionally used in the field under consideration, and, for example, from about 0.01 to 20% relative to the total weight of the composition. Depending on their nature, these adjuvants can be introduced into the fatty phase, into the aqueous phase and/or into the lipid vesicles.

Active agents which may be mentioned in particular are moisturizers and, for example, protein hydrolysates and polyols such as glycerol, glycols such as polyethylene glycols, and sugar derivatives.

The active agent(s) can be present, for example, in a concentration ranging from about 0.01 to 20%, preferably from about 0.1 to 5% and more preferably from about 0.5 to 3%, relative to the total weight of the composition.

Having described the present invention reference will now be made to certain examples which are provided solely for purposes of illustration and are not intended to be limitative. The amounts therein are given as percentages by weight, except where otherwise mentioned.

EXAMPLE 1

Protective Cream

A. Oily Phase
  Cetyldimethicone copolyol/polyglyceryl-4 isostearate/hexyl laurate (Abil WE 09 sold by Goldschmidt) 4%
  Hydrogenated jojoba oil 5.2%
  Volatile silicone oil (cyclohexadimethylsiloxane) 2.2%
  Polyethylene wax 0.8%
  Cetaryl octanoate/isopropyl myristate (oils) 7%
  Nylon 12 0.8%
B. Aqueous phase
  Sodium chloride 0.5%
  Glycerol 2%
  Water qs 100%
C. Impasting
  Polyamide fibers (Polyamide 0.9 Dtex, 0.3 mm—Paul Bonte company) 8%
  Silicone gum 1.3%
  Trifluoromethyl alkyldimethicone (X-22-819, Shin Etsu, wetting agent) 1.6%
  Pigments 0.1%

Procedure: The oily phase is heated without the volatile silicone until the phase is homogeneous. Separately, the aqueous phase is heated to the same temperature. The emulsion is prepared by pouring the aqueous phase into the oily phase, followed by adding the volatile silicone. Next, phase C is added and the 5 mixture is cooled.

A protective tinted cream is obtained.

EXAMPLE 2

Moisturizing Cream

A. Oily Phase
  Cetyldimethicone copolyol/polyglyceryl-4 isostearate/hexyl laurate (Abil WE 09 sold by Goldschmidt) 5%
  Hydrogenated jojoba oil 5.5%
  Volatile silicone oil (cyclohexadimethylsiloxane) 7.3%
  Polyethylene wax 0.8%
  Cetaryl octanoate/isopropyl myristate (oils) 7%
  Nylon 12 0.8%
B. Aqueous Phase
  chloride 0.5%
  Glycerol 2%
  Water qs 100%
C. Impasting
  Polyamide fibers (Polyamide 0.9 Dtex, 0.3 mm—Paul Bonte company) 8%
  Fluorosilicone oil (fluoropropyl dimethylsiloxane) (X-22-819 sold by the company Shin-Etsu) 1.6%
  Crosslinked polyorganosiloxane containing 24% active material in non-volatile PDMS (KSG 16) 2.1%

Procedure: The oily phase is heated without the volatile silicone until the phase is homogeneous. Separately, the aqueous phase is heated to the same temperature. The emulsion is prepared by pouring the aqueous phase into the oily phase, followed by adding the volatile silicone. Next, phase C is added and the mixture is cooled.

A white cream which is capable of moisturizing the skin is obtained.

EXAMPLE 3

Cast Emulsion

A. Oily Phase
  Cetyldimethicone copolyol/polyglyceryl-4isostearate/hexyl laurate (Abil WE 09 sold by Goldschmidt) 45%
  Hydrogenated jojoba oil 5.5%
  Volatile silicone oil (cyclohexadimethylsiloxane) 7.3%
  Polyethylene wax 0.8
  Cetaryl octanoate/isopropyl myristate (oils) 7%
  Bentone 2.1%
B. Aqueous Phase
  Sodium chloride 0.5%
  Glycerol 2%
  Water qs 100%
C. Impasting
  Polyamide fibers (Polyamide 0.9 Dtex, 0.3 mm—Paul Bonte company) 8%
  Fluorosilicone oil (fluoropropyl dimethyl-siloxane) (X-22-819 sold by the company Shin-Etsu) 1.6%
  Crosslinked polyorganosiloxane containing 24% active material in non-volatile PDMS (KSG 16) 2.1%

Procedure: The oily phase is heated without the volatile silicone until the phase is homogeneous. Separately, the aqueous phase is heated to the same temperature. The emulsion is prepared by pouring the aqueous phase into the oily phase, followed by adding the volatile silicone. Next, phase C is added and the mixture is cooled.

A white cream which is capable of protecting the skin is obtained.

The emulsion and composition containing the same of the present invention may be used as described above with all mammals, however, they are particularly advantageous as used for and by humans. The emulsion and compositions containing the same may be applied manually to the hair, skin or-lips or directly thereto from a container or other dispenser.

Having described the present invention, it will now be readily apparent to one skilled in the art that many changes and modifications may be made to the above-described embodiments without departing from the spirit and the scope of the present invention.

What is claimed is:

1. A composition in emulsion form, which does not dephase for at least 2 months at 45° C., comprising, in a physiologically acceptable medium, an aqueous phase dispersed in an oily phase, which contains fibers, at least one silicone surfactant, and at least one wax.

2. The composition of claim 1, wherein said fibers are inorganic or organic.

3. The composition of claim 1, wherein the fibers are selected from the group consisting of silk, cotton, wool fibers, flax fibers, cellulose fibers extracted from wood or plants or algae, polyamide, rayon fibers, viscose fibers, acetate fibers, poly-p-phenylene terephthamide fibers, acrylic fibers, polyolefin fibers, glass fibers, silica fibers, aramid fibers, carbon fibers, polytetrafluoroethylene, insoluble collagen, polyester, polyvinyl chloride, polyvinylidene chloride, polyvinyl alcohol, polyacrylonitrile, chitosan, polyurethane fibers, polyethylene phthalate fibers, fibers from mixtures of polymers, surgical fibers, and mixtures thereof.

4. The composition of claim 3, wherein said acetate fibers are selected from the group consisting of rayon acetate fibers, cellulose acetate fibers, and silk acetate fibers.

5. The composition of claim 3, wherein said fibers are carbon fibers.

6. The composition of claim 3, wherein said acrylic fibers are selected from the group consisting of polymethyl methacrylate and poly-2-hydroxyethyl methacrylate fibers.

7. The composition of claim 3, wherein said polyolefin fibers are selected from the group consisting of polyethylene and polypropylene fibers.

8. The composition of claim 1, wherein the fibers are fibers of synthetic origin.

9. The composition of claim 1, wherein the fibers are polyamide fibers or poly-p-phenylene terephthamide fibers.

10. The composition of claim 1, wherein the fibers have a length ranging from about 0.1 to 1.5 mm.

11. The composition of claim 1, wherein the fibers have an average diameter ranging from about 5 to 50 µm.

12. The composition of claim 1, wherein the fibers are present in an amount ranging from about 0.1 to 20% by weight relative to the total weight of the composition.

13. The composition of claim 1, wherein the silicone surfactant is selected from the group consisting of alkyl- and alkoxydimethicone copolyols.

14. The composition of claim 1, wherein the amount of silicone surfactant ranges from about 0.1 to 5% by weight of active material relative to the total weight of the composition.

15. The composition of claim 1, wherein the wax is selected from the group consisting of waxes of animal origin, waxes of plant origin, mineral waxes, synthetic waxes, silicone waxes, hydrogenated oils that are solid at 25° C., and mixtures thereof.

16. The composition of claim 1, wherein the amount of wax(es) ranges from about 0.5 to 10% by weight relative to the total weight of the composition.

17. The composition of claim 1, wherein the oily phase is present in an amount ranging from about 10 to 50% by weight relative to the total weight of the composition.

18. The composition of claim 1, wherein the oily phase contains at least one silicone oil.

19. The composition of claim 1, which is a cosmetic or dermatological composition.

20. The composition of claim 1, wherein oily phase further comprises oils of plant origin, mineral oils, synthetic oils, volatile or non-volatile silicone oils, or fluorosilicone oils.

21. The composition of claim 1, which further comprises moisturizers, preserving agents, antioxidants, complexing agents, pH modifiers, fragrances, fillers, bactericides, odor absorbers, dyestuffs or lipid vesicles.

22. A method-for treating, protecting, caring for, removing make-up from or cleansing the skin, the lips or the hair, or for making up the skin or the lips or a combination thereof, of a human which comprises administering an effective amount of the composition of claim 1, to said skin, lips or hair or any combination thereof of said human.

23. The method of claim 22, which comprises treating the skin.

24. The method of claim 22, which comprises removing-make-up from the skin or lips.

25. The method of claim 22, which comprises making-up the skin or lip.

26. The method of claim 22, which comprises treating the hair.

27. The method of claim 23, wherein said treating comprises sun-protecting.

28. The method of claim 23, wherein said skin is dry skin.

* * * * *

UNITED STATES PATENT AND TRADEMARK OFFICE
CERTIFICATE OF CORRECTION

PATENT NO. : 6,503,520 B1  Page 1 of 1
DATED : January 7, 2003
INVENTOR(S) : Isabelle Afriat It is certified that error appears in the above-identified patent and that said Letters Patent is hereby corrected as shown below:

Column 8,
Line 27, "method-for" should read -- method for --;
Line 35, "removing-" should read -- removing --.

Signed and Sealed this

Twenty-second Day of April, 2003

JAMES E. ROGAN
*Director of the United States Patent and Trademark Office*